United States Patent
Cowan (10) Patent No.: US 9,351,865 B2
(45) Date of Patent: May 31, 2016

(54) APPARATUS FOR PLANTAR FASCIITIS TREATMENT AND METHOD FOR MAKING SAME

(71) Applicant: Charles G. Cowan, Lake Placid, NY (US)

(72) Inventor: Charles G. Cowan, Lake Placid, NY (US)

( * ) Notice: Subject to any disclaimer, the term of this patent is extended or adjusted under 35 U.S.C. 154(b) by 206 days.

(21) Appl. No.: 13/768,408

(22) Filed: Feb. 15, 2013

(65) Prior Publication Data

US 2013/0218061 A1    Aug. 22, 2013

Related U.S. Application Data

(60) Provisional application No. 61/600,209, filed on Feb. 17, 2012.

(51) Int. Cl.
*A61F 5/00* (2006.01)
*A61F 5/01* (2006.01)

(52) U.S. Cl.
CPC ............. *A61F 5/0127* (2013.01); *A61F 5/0111* (2013.01)

(58) Field of Classification Search
CPC ....... A61F 13/065; A61F 13/066; A61F 5/01; A61F 5/004; A61F 5/011; A61F 5/0127; A61F 13/064; A43B 19/00
USPC ................ 602/23, 5, 60–66, 27–29; 128/882; 5/650, 651
See application file for complete search history.

(56) References Cited

U.S. PATENT DOCUMENTS

| | | | | |
|---|---|---|---|---|
| 1,025,571 A | * | 5/1912 | Howe | A61F 13/065 602/66 |
| 1,318,971 A | * | 10/1919 | Cook | H01J 19/42 313/243 |
| 1,492,514 A | * | 4/1924 | Jensen | A61F 13/065 602/66 |
| 1,512,218 A | * | 10/1924 | Goldsmith | A61F 13/065 602/66 |
| 1,538,026 A | * | 5/1925 | Cramer | A61F 13/065 602/66 |
| 1,577,203 A | * | 3/1926 | Cramer | A61F 13/065 602/66 |
| 1,651,285 A | * | 11/1927 | Levick, Jr. | A61F 13/065 602/66 |
| 1,684,948 A | * | 9/1928 | Degling | A61F 13/065 602/66 |
| 1,767,263 A | * | 6/1930 | Scholl | A61F 13/065 602/66 |

(Continued)

FOREIGN PATENT DOCUMENTS

FR    2643255 A3  *  8/1990

OTHER PUBLICATIONS

Pro-Tech Athletics, Product Description for Arch Pro-Tech Arch Supports, pro-tecathletics.com, downloaded on Feb. 15, 2013.

(Continued)

*Primary Examiner* — Kim Lewis
(74) *Attorney, Agent, or Firm* — Sheehan Phinney Bass & Green PA (57) ABSTRACT

A plantar fasciitis arch support (PFAS) device is presented. The PFAS device is an ergonomic compression device that administers a measured pressure along the tissue on the plantar surface of the foot for purpose of relieving the pain and inflammation of plantar fasciitis. The device works by directly compressing and stretching the plantar fascia in order to relieve pressure at the plantar fascia attachment points. This device differs from current conventional splints that use a dorsiflexion force of the foot and ankle complex to stretch the plantar fascia and Achilles tendon. The device is small, affordable, lightweight, and comfortable to wear. It targets the fascia directly, stretching the tendon gently through the night rather than indirectly stretching the calf or Achilles tendon.

25 Claims, 6 Drawing Sheets

(56) References Cited

U.S. PATENT DOCUMENTS

| | | | |
|---|---|---|---|
| 2,633,130 A * | 3/1953 | Scholl | A61F 13/065 |
| | | | 602/66 |
| 5,399,195 A | 3/1995 | Strasberg et al. | |
| 5,545,129 A * | 8/1996 | Snook | A61F 13/067 |
| | | | 128/894 |
| 5,799,659 A | 9/1998 | Stano et al. | |
| 6,019,741 A | 2/2000 | Prieskorn | |
| 6,699,209 B2 * | 3/2004 | Turtzo | 602/27 |
| 6,804,902 B1 | 10/2004 | McCracken et al. | |
| 6,886,276 B2 * | 5/2005 | Hlavac | 36/166 |
| 7,572,241 B2 | 8/2009 | Slautterback et al. | |
| 7,753,864 B2 | 7/2010 | Beckwith et al. | |
| 2004/0215123 A1 * | 10/2004 | Slautterback et al. | 602/27 |
| 2009/0024066 A1 * | 1/2009 | Sorg | A43B 7/1425 |
| | | | 602/27 |
| 2010/0249685 A1 * | 9/2010 | Llorens et al. | 602/28 |

OTHER PUBLICATIONS

Pro-Tech Athletics, Product Description for Achilles Tendon Support, pro-tecathletics.com, downloaded on Feb. 15, 2013.

Pro-Tech Athletics, Product Description for Pro-Tec Night Splint, pro-tecathletics.com, downloaded on Feb. 15, 2013.

Pro-Tech Athletics, Product Description for Metatarsal Lift Compression Pads, pro-tecathletics.com, downloaded on Feb. 15, 2013.

* cited by examiner

APPARATUS FOR PLANTAR FASCIITIS TREATMENT AND METHOD FOR MAKING SAME

CROSS-REFERENCE TO RELATED APPLICATIONS

This application claims the benefit of U.S. Provisional Patent Application Ser. No. 61/600,209, filed Feb. 17, 2012, entitled "APPARATUS FOR PLANTAR FASCIITIS TREATMENT AND METHOD FOR MAKING SAME," which is incorporated by reference herein in its entirety.

FIELD OF THE INVENTION

This invention relates to the field of orthotic devices, and in particular, to a plantar fascia compression device.

BACKGROUND OF THE INVENTION

Plantar fasciitis is inflammation of the thick, elastic tissue (plantar fascia) located in the sole of the foot. The plantar fascia connects the heel bone (calcaneus) to the base of the toes (metatarsophalangeal joints), creating the soft tissue support of the arch of the foot. Generally, inflammation occurs when the plantar fascia is overstretched or overused. Inflammation causes sharp or dull pain and/or stiffness at the bottom of the heel. Although regular daytime movement may stretch the fascia and ease the pain of the sufferer, during seep the foot relaxes and the plantar fascia contracts. Because the tendon remains static for multiple hours, it binds and develops scar tissue. In the morning during the initial weight-bearing steps, the plantar fascia of the sufferer may be stretched abruptly, thereby tearing the scar tissue. This cycle of plantar fascia binding and tearing is a primary source of pain to the sufferer and prolongs the healing process.

Risk factors for plantar fasciitis include: arch problems wherein both flat feet and high arches are risk factors; obesity or rapid and/or sudden weight gain; long-distance running; long-term pressure to the arches, as in the cases of those in the food-service industry; tight Achilles tendons (the tendon which connects the calf muscle to the heel); and shoes with poor arch support or weak soles. According to the National Institute of Health, plantar fasciitis most commonly affects men ages 40-70. An article in the Journal of Bone and Joint Surgery claims that two million Americans are affected annually, and ten percent of the population suffers from plantar fasciitis in their lifetimes.

Options for treatment and prevention of plantar fasciitis include, but are not limited to:

1) stretching of the calf muscles, the Achilles tendon, the arches, and the plantar fascia, both with and without the use of devices;
2) rest;
3) direct application of ice;
4) use of daytime orthotics (foot supporters);
5) use of non-steroidal anti-inflammatory drugs;
6) local injection of corticosteroids; and
7) administration of extracorporeal shockwave therapy.

Generally, a tailored prescription of one or more of the above treatments may improve the pain associated with plantar fasciitis. Patients and healthcare professionals generally allow between three months and two years for the symptoms to improve. Plantar fasciitis is considered a curable condition, with the median of patients noticing improvement in nine months. Rarely, surgery is necessary for relief from plantar fasciitis. A number of specific treatment methods proposed in the prior art for treating plantar fasciitis, include the following.

U.S. Pat. No. 5,399,155 issued to Strassburg, et al. discloses a Static ankle plantar-flexion prevention device, now widely marketed as the Strassburg Sock. The device is designed to hold the plantar fascia "in a neutral to slight dorsiflexion by means of passive static tension, thus not allowing it to contract." The device was designed with an "over the calf sock . . . a reinforced adjustable support strap . . . a reinforced inelastic adjustable strap attached to the toe of the sock." The device was designed with simplicity in mind and allows for ankle movement. The invention is recommended for nighttime use and during periods of inactivity.

U.S. Pat. No. 5,799,659 issued to Stano discloses an Ankle foot orthosis night splint with orthowedge. Proposed as an inexpensive orthosis "for the treatment of foot and ankle conditions including Plantar fasciitis and tendonitis, the orthosis is a rigid, molded shell manufactured in a variety of incremental sizes, having a generally U-shaped cross-sectional configuration and a flat foot bed, covered by a soft fabric covering, and using a removable and interchangeable foot bed wedge insert permitting the angle of dorsiflexion, plantarflexion, inversion and eversion to be varied." This prototype was a pioneer in the field of night-splints, which since has broadened to include a variety of models.

U.S. Pat. No. 6,019,741 issued to Prieskorn discloses an orthopedic foot splint with a "rigid brace adapted to be worn on the front of the lower leg while leaving the rear of the leg, ankle and heel uncovered." This variation to the invention of Stano is designed to increase night-time comfort "because there is no rigid structure to come between the patient's leg or foot and a mattress or other surface on which the leg may be resting," but still requires the brace to extend up the leg, stretching the Achilles tendon.

U.S. Pat. No. 6,804,902 issued to McCracken discloses an Adjustable arch support orthosis including a "variably tensioned arch curve and method of utilizing orthosis." In order to support the arch and foot of the user, "the arch support orthosis includes a metatarsal curve, a curved heel portion and a continuous medial longitudinal arch curve." Designed for both "weighted and unweighted use," the device allows the user to adjust the tension along the arch curve in order to treat foot and arch disorders, including plantar fasciitis. This development attempts to use fewer rigid materials in order to stretch the calf, but the device requires a strap on the lower leg and maintains a stretch to the Achilles tendon.

U.S. Pat. No. 7,572,241 issued to Slautterback, et al. discloses an orthopedic night foot splint which "maintains the wearer's foot . . . in a pre-selected amount of dorsiflexion." The splint is designed with a footplate, a bracket attached at the heel region, a "strut . . . extending along the lower leg of the wearer," and a strut sleeve. The device is fully adjustable and "provides a comfortable 'slipper-like' feel for the wearer." Again, the comfort is emphasized, but this device requires the calf to be engaged.

U.S. Pat. No. 7,753,864 issued to Beckwith discloses a Foot support device designed with a "calf strap removably engagable to the calf of a leg, a foot assembly removably engagable to the foot . . . and a substantially inelastic tension member connectable between the calf strap and the foot." This device was designed to hold the plantar surface of the foot "in a neutral to slight dorsiflection." Again, though the plantar surface is held in "slight dorsiflection (sic)," the calf is engaged.

Therefore, there is a need to address some or all of the abovementioned shortcomings.

SUMMARY OF THE INVENTION

Embodiments of the present invention provide an apparatus for plantar faciitis treatment and a method for making such an apparatus. Briefly described, a first aspect of the present invention is directed to a foot wearable ergonomic compression device. The device includes a compressible block with a top. The top includes a heel contact region and a metatarsophalangeal contact region. The device includes a base substantially opposite the top, a first side disposed substantially adjacent the top and the base, and a second side opposite the first side disposed substantially adjacent the top and the base. A strap is attached to the compressible block, wherein the strap is configured to hold the compressible block top adjacent to the foot.

A second aspect of the present invention is directed to a foot wearable ergonomic compression device. The device includes a compressible block with a top. The top includes a heel contact region and a metatarsophalangeal contact region. The device includes a base substantially opposite the top, a first side disposed substantially adjacent the top and the base, and a second side opposite the first side disposed substantially adjacent the top and the base. A first strap portion is attached to the first side, and a second strap portion attached to the second side. The first strap portion and the second strap portion are configured to wrap around the foot. The first strap portion is configured to attach to the second strap portion, holding the compressible block top adjacent to the sole of the foot.

Briefly described, a third aspect of the present invention is directed to a method for manufacturing a foot wearable ergonomic compression device. The method includes the steps of forming a substantially rectangular compressible block, wherein the block is sized to extend from the ball of the foot to the heel of the foot, forming a first edge and a second edge of the block, wherein the first edge corresponds to the ball of the foot, and the second edge corresponds to the heel of the foot, and forming a strap of material sized to surround the foot and the block held adjacent to a sole of the foot.

An object of the present invention is to provide a plantar fascia compression device for effectively treating and preventing plantar fasciitis.

A further object of the present invention is to provide a plantar fascia compression device that is compact, portable, easy to use, affordable, and more comfortable than current conventional treatments, to encourage compliance.

A further object of the present invention is to provide a plantar fascia compression device that directly stretches the plantar fascia over an extended period of time, as opposed to nighttime alternatives which attempt to treat and prevent plantar fasciitis by stretching the calf muscle or the Achilles tendon rather than the source of the pain, the plantar fascia itself.

A further object of the present invention is to provide a plantar fascia compression device that eases the pain of the first, and usually the most painful, morning steps of plantar fasciitis sufferers. The device is smaller, easier to use, more directly targeted towards stretching the plantar fascia and more comfortable than current conventional treatments. It is an ergonomic compression device that administers a measured pressure substantially along the tissue on the plantar surface of the foot for purpose of pain and inflammation relief.

A further object of the present invention is to relieve pressure at the attachment points of the plantar fasciitis, particularly at the heel.

According to one aspect of the invention, a plantar fascia compression device is provided, having a block encased lengthwise with fabric, which is adapted to support the arch, specifically along and/or beyond the space between the calcaneus and the metatarsal head. The curved edges of the top of the block are curved to engage the plantar fascia at both the calcaneus and the metatarsal head in a compression and stretch designed to lengthen the plantar fascia. Alternatively, the curved edges may engage the foot slightly beyond the calcaneus and the metatarsal head to relieve stress upon the attachment points. Since the irritation of those suffering from plantar fasciitis occurs directly on the ends of the fascia, this device directly targets those sources of irritation. A strap holding the block against the foot of the wearer may be tightened over the course of use, thus deepening the stretch over time.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

DETAILED DESCRIPTION OF THE INVENTION

Reference will now be made in detail to embodiments of the present invention, examples of which are illustrated in the accompanying drawings. Exemplary embodiments of a plantar fasciitis arch support (PFAS) device for the treatment and prevention of plantar fasciitis according to the invention are described in detail. Wherever possible, the same reference numbers are used in the drawings and the description to refer to the same or like parts.

An exemplary embodiment of a device for treating and preventing plantar fasciitis includes a flat-based, curved-top block that is positioned beneath the foot at the arch and is fitted at or near the points where the fascia attaches to the bone. The block is cut with a flat top surface and curved at the edges to provide a gentle but definite compression and stretch to the heel-end of the plantar fascia, the point that is generally the source of pain for plantar fasciitis sufferers. The block is affixed to the base of the foot with the aid of a closed cell foam strap, which is wrapped around the foot and affixed with a hook-and loop type adhesive.

Figure 1:
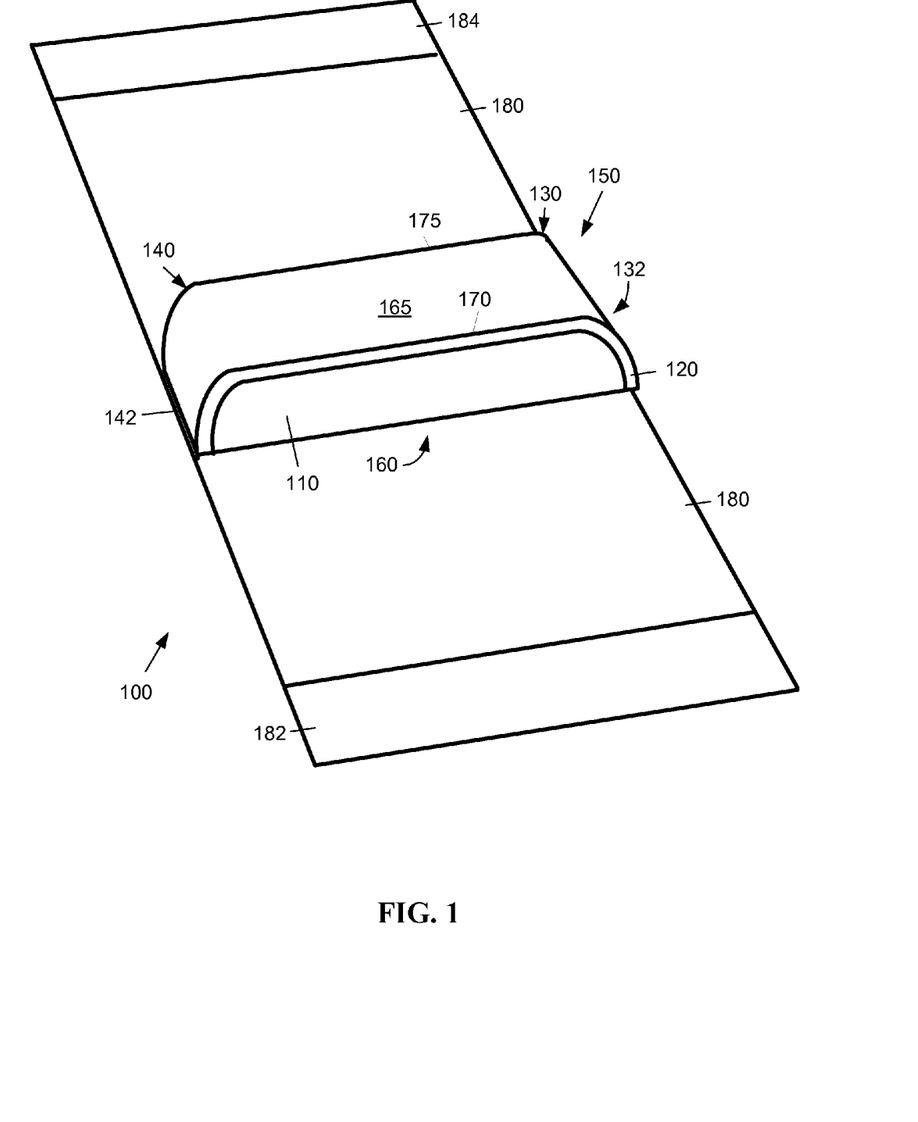
FIG. 1 is schematic diagram of a first exemplary embodiment of a plantar fasciitis arch support device.

Under a first embodiment, as shown by FIG. 1, the PFAS device 100 includes a block 150 that has no moving parts, and the block 150 is generally placed against a foot, between the metatarsal head and the calcaneus of the wearer. The block 150 has a top surface 165 with a first curved top edge 130 and a second curved top edge 140. The gentle curves on the first curved top edge 130 and the second curved top edge 140 may promote a gradual, gentle compression that makes the PFAS device 100 comfortable to wear for long periods of time, thereby increasing the effectiveness of the PFAS device 100. The first curved top edge 130 and the second curved top edge 140 are shaped to provide a larger area of contact against the attachment point of the plantar fasciitis than would be provided by, for example, a block 150 with square edges. Similarly, the first top curved edge 130 and the second curved top edge 140 may be shaped to provide adequate pressure upon the plantar fasciitis attachment points while being comfortable enough to wear while sleeping. The first and second top edges 130, 140 may be formed according the needs of specific applications, for example, a sharp curve to apply higher pressure to a small contact area, or a gently rounded curve to distribute pressure over a larger contact area. The shape of the first curve 130 may be different from the shape of the second curve 140.

While the block 150 may be sized such that the first top curved edge 130 and the second curved top edge 140 may be located substantially at the plantar fasciitis attachment points, the block 150 may also be sized and/or positioned so the first top curved edge 130 and the second curved top edge 140 contact the foot at points near, but not actually at the attachment points. For example, the first top curved edge 130 and the second curved top edge 140 may contact the foot slightly beyond each plantar fasciitis attachment point, such that pressure is not applied directly upon the attachment points.

A base 160 of the block 150 may be substantially flat with no curved corners, providing an even surface, for example for the wearer of the PEAS device 100 to walk or stand upon. Under the first embodiment, the block 150 may be made of a single compressible material, for example, formed of closed cell foam. Other compressible materials may also be used, for example, open-cell foam. The compressibility of the material may serve to provide consistent pressure to the ends of the plantar fasciitis when the block 150 is held in place against a foot. The material should be sufficiently rigid to provide structure for applying consistent pressure at the first and second top edges 130, 140.

The flat base 160 of the block 150 provides even distribution of force across the block 150 when the base 160 of the block 150 is used to hold the block 150 in place against the foot of a wearer. In addition, a flat base 160 of the block 150 may provide other advantages, such as a stable surface so that the wearer may stand or walk while wearing the HAS device. However, there is no objection to the base 160 of block 150 being curved, for example, a concave curve or a convex curve. It should be noted that the PFAS device 100 is not generally recommended for use while walking more than short distances.

Under the first embodiment, the block 150 includes a substantially solid compressible core 110 encased by a flexible fabric strip 120. The fabric strip 120 may be permanently adhered to the solid core 110, for example using glue or other adhesives. Alternatively, the fabric, strip 120 may be removably adhered to the solid core 110. A removable fabric strip 120 may facilitate replacement of the fabric strip 120 when it becomes worn or soiled. The fabric used for the fabric strip 120 may breathable and comfortable and may adhere to itself. The fabric of the fabric strip 120 may also have cushioning properties, or may be a composite of a fabric and a cushion, for example, an elastic cloth layered with foam or sponge. The fabric strip 120 may entirely enclose the solid core 110, or may leave portions of the solid core 110 exposed. For example, the fabric strip 120 may wrap around the solid core 110 lengthwise, so that the base surface 160, the first top edge 130, and the second top edge 140 are encased, leaving the slides of the solid core 110 exposed.

A strap 180 attaching to the block 150 may be formed of fabric, preferably with some elastic properties, for example, neoprene or ace bandage. The strap 180 has a first strap attachment region 182 at a first end of the strap 180, and a second strap attachment region 184 at a second end of the strap 180. In general, the first attachment region 182 may attach to the second attachment region 184 when worn around the foot of a wearer. However, there may be embodiments with only a single strap attachment region 182 configured to attach to any other portion of the strap 180, or two attachment regions 182, 184 that do not attach directly to one another, but instead to other portions of the strap 180, or to an intervening attachment portion (not shown), for example laces or a secondary strap.

The strap 180 may alternatively be configured to just extend from a first side 170 of the block 150, wrap around the foot and attach to a second side 175 of the block 150. In each of these configurations, the strap 180 may generally be sized to match to the length of the block 150, where the strap 180 is wrapped around the block 150 and the foot, and the ends of strap 180 may be adhered together in order to hold the block 150 in place against the foot.

The adhering of the ends 182, 184 of the strap 180 may be accomplished by several means familiar to those having ordinary skill in the art, including, but not limited to, hook and loop fasteners, ace bandage clips, snaps, buckles, laces and loopholes, strap harnesses, buttons, and the like. The strap 180 may be adjusted to loosen or tighten the block 150 against the foot. Tightening the strap 180 increases the compression to the heel-end of the plantar fascia, and a gradual tightening over a period of hours or days may help the user to achieve a desired compression and resulting stretch of the plantar fascia for effective treatment of plantar fasciitis.

As used within this document, the length of the block 150 refers to the distance between a first end 132 and a second end 142, corresponding to the ends of the block 150 contacting the heel and the ball of the foot. The thickness of the block 150 refers to the distance between the top surface 165 and the base 160 of the block 150. The width of the block 150 refers to the distance between the first side 170 and the second side 175 of the block 150.

As shown by FIG. 1, the shape of the block 150 and/or top surface 165 may be substantially rectangular, with the first side 170 and the second side 175 being substantially straight and parallel. The width of the block 150 may be configured to substantially match the width of the foot of a wearer at the widest portion of the foot. It may be desirable for the width of the block 150 to be substantially similar to the width of the foot of the wearer, but there are no objections to having block 150 with a wider or narrower width. There is also no objection to other shapes, for example, an elongated trapezoid shape where the width of the first end 132 of the block 150 may be narrower or wider than the second end 142 of the block 150.

While FIG. 1 shows the thickness of the block 150 as being substantially uniform between the top surface 165 and the base 160 between the first top curved edge 130 and the second curved top edge 140, there is no objection to variations in thickness, for example, with the block 150 having a substantially wedge shape side profile where the block 150 is thicker or thinner at the first top curved edge 130 than at the second curved top edge 140. Similarly, while the thickness of the block from the top surface 165 and the base 160 between the first top curved edge 130 and the second curved top edge 140 is depicted as being substantially flat, there is no objection to other configurations, for example, thickening the middle portion between the first top curved edge 130 and the second curved top edge 140 to provide some arch support, or thinning in the middle portion to provide additional clearance between the block 150 and the foot.

Furthermore, it should be noted that while FIG. 1 depicts various aspects of the PFAS device 100, it is not intended to be to scale, particularly regarding the length of the strap 180 in relation to the size of the block 150.

Figure 2A:
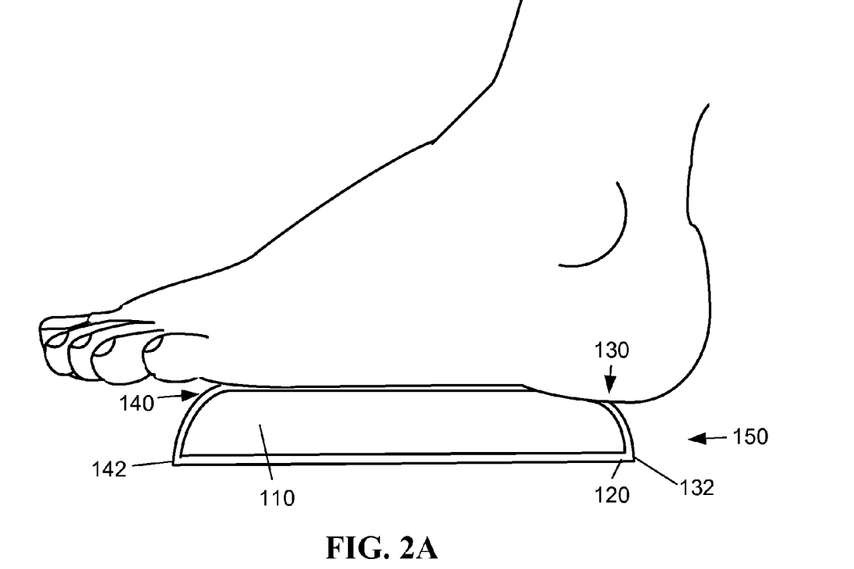
FIG. 2A is schematic diagram of a first side view of the first exemplary embodiment of a plantar fasciitis arch support device.
Figure 2B:
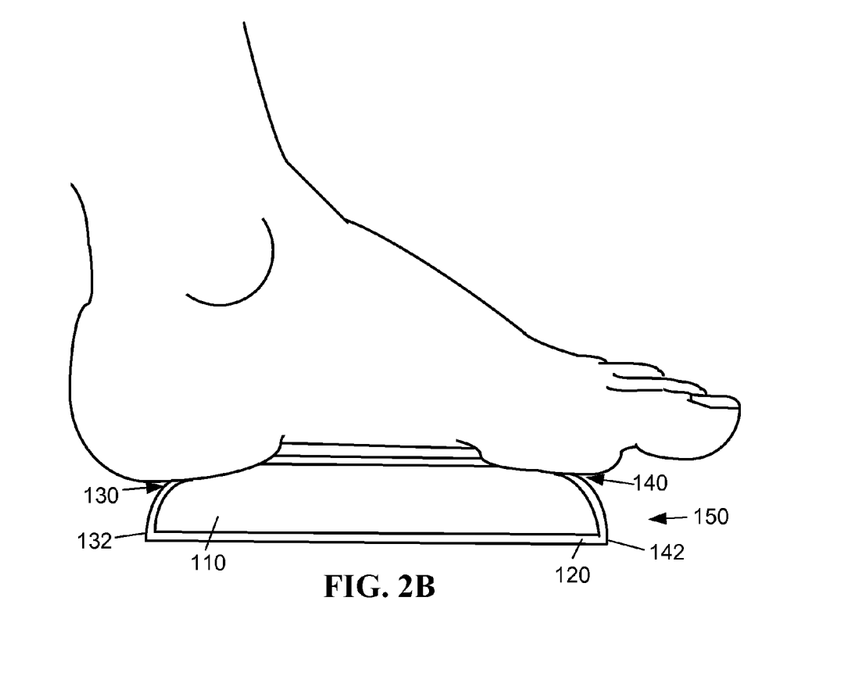
FIG. 2B is schematic diagram of a second side view of the first embodiment of a plantar fasciitis arch support device.
Figure 3:
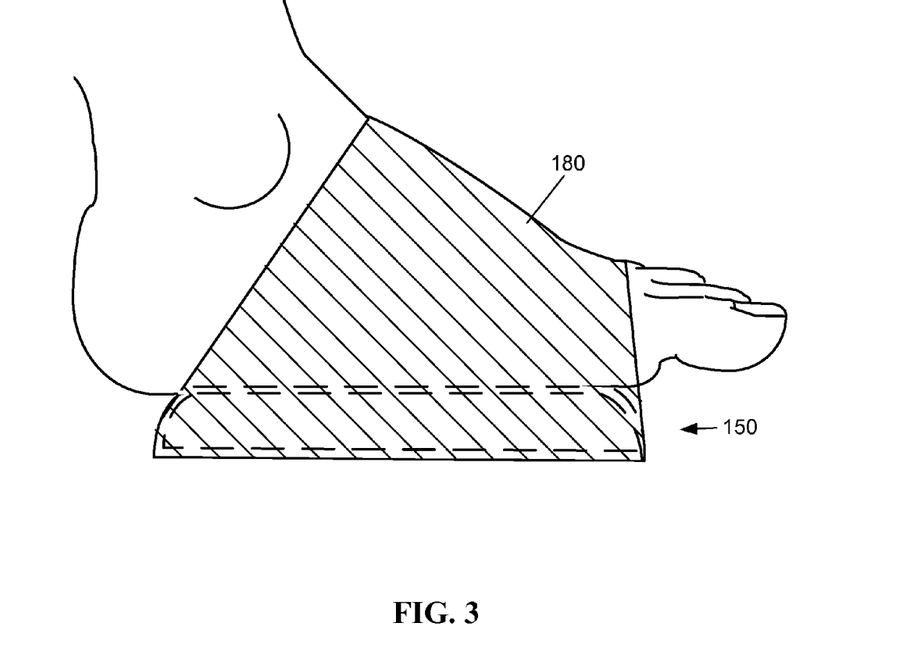
FIG. 3 is schematic diagram of the first exemplary embodiment of a plantar fasciitis arch support device strapped to a foot.

FIG. 2A shows the positioning of the block 150 against a foot from a first view, while FIG. 2B shows the positioning of the block 150 against a foot from a second view. It should be noted that the strap 180 is omitted from FIGS. 2A and 2B for clarity. As shown by FIG. 3, PFAS device 100 including the block 150, having the solid core 110 encased by the fabric strip 120, is held in place against the foot with the strap 180. As shown by FIGS. 2A and 2B, the block 150 may have a length substantially shorter that the length of the foot of the wearer, so that the foot overhands the ends of the block 150 past the first curved top edge 130 and/or the second curved top edge 140. Of course, other lengths are also possible, where the first end 132 and/or the second end 142 may extend up to or beyond the foot of the wearer. The length may be tailored to suit the wearer, so that contact between the foot and the block 150 occurs in areas most beneficial to the wearer.

Under a second embodiment, the solid core 110 may be made or partially made of a hard material that does not appreciably compress under the weight of the wearer, for example, a block of wood or plastic. Under the second embodiment, the fabric strip 120 may be compressible, for example a foam rubber ribbon, so the fabric strip 120 provides compression, while the solid core 110 provides structural support. The strap 180 may wrap around the foot and the block 150 as per the first embodiment. The solid core 110 may be formed of a composite of compressible and non-compressible materials, so pressure is applied at or near the plantar fasciitis attachments points, but less pressure is applied elsewhere upon the foot, providing more comfort and aiding in circulation.

Under a third embodiment the block 150 is formed of a composite material, thereby incorporating the functions of the fabric strip 120 and the solid core 110 of the first and second embodiments into a self-contained structure, making a separate fabric strip 120 unnecessary. As with the second embodiment, under the third embodiment the block 150 is formed of a composite of compressible and non-compressible materials, so pressure is applied at or near the plantar fasciitis attachments points, but less pressure is applied elsewhere upon the foot, providing more comfort and aiding in circulation.

Figure 5:
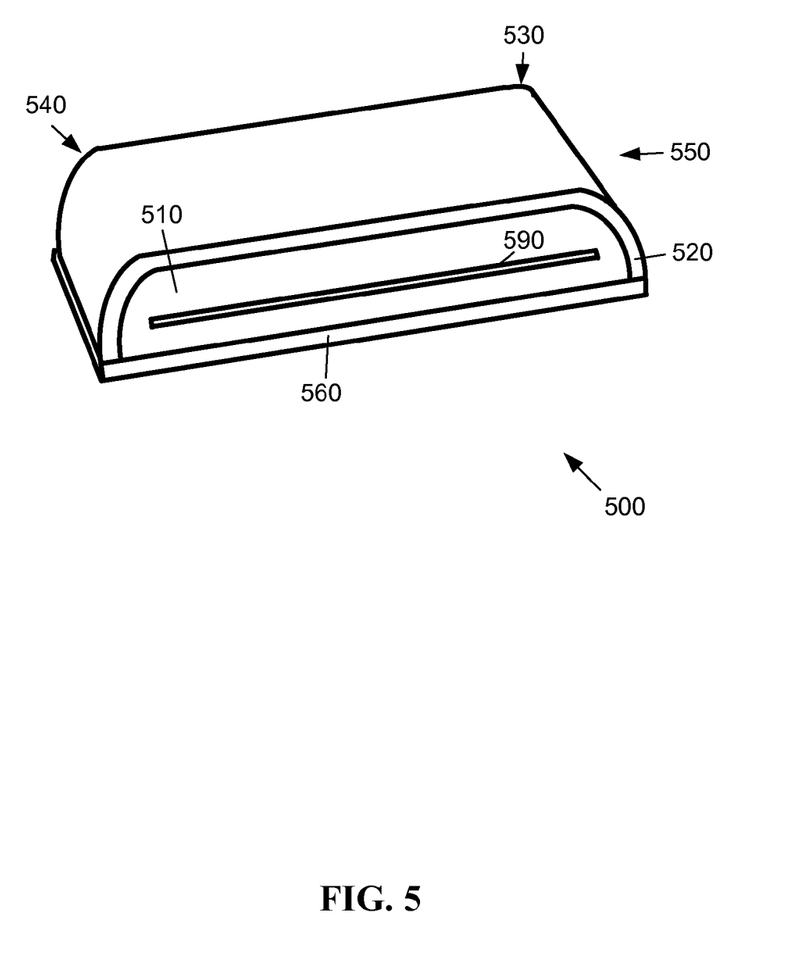
FIG. 5 is schematic diagram of a fourth exemplary embodiment of a plantar fasciitis arch support device.

Additional embodiments are also possible. For example, under a fourth embodiment 500, as shown by FIG. 5, a strap (not shown) may pass through a slot or aperture 590 in a block 550, rather than attaching to the outside the block 550 and/or a fabric strip 520 partially or completely wrapping a solid core 510. The strap may be able to freely slide through the slot 590, held in place substantially by friction between the strap and the block 550, and/or the weight of the wearer compressing the slot 590 to hold the strap substantially in place. However, there is no objection to using means to prevent the strap from sliding in the slot 590, for example, using protrusions such as pins or pegs within the slot 590 passing through holes in the strap to hold the strap in place. Of course, other similar means may be used by persons having ordinary skill in the art to hold the strap substantially in place within the slot 590.

Under the fourth embodiment 500, the base of the block 550 may include a bottom layer 560 to prevent the wearer slipping on the floor, for example, a region of non-skid material, such as rubber, below the base of the block 550, where the fabric strip 520 encloses the top surface, the first top edge 530 and the second top edge 540, but not the bottom layer 560.

Similarly, under a fifth embodiment (not shown), a strap may not pass under or through the block 550, but instead may be made of two sections, with a first section attaching to a first side of the block 550, and a second section attaching to a second side of the block 550. The fifth embodiment may be substantially similar to the fourth embodiment, except under the fifth embodiment, the first section and the second section of the strap may be removably attached to the block 550. For example, the first section and the second section of the strap may be removably attached to the block 550 by fasteners such as snaps or buttons, or other fasteners known to persons having ordinary skill in the art. However, there is no objection to the first section and the second section of the strap being non-removably attached to the block 550, for example, by gluing or sewing the first section and the second section of the strap to the block 550.

While several of the above embodiments describe a single wide strap holding a compressible block against the foot of a wearer, there is no objection to instead using two or more narrower straps to hold the block in place. For example, a first strap may be positioned close to the heel portion of the block, and a second strap may be positioned close to the ball portion of the block. Such a configuration may be advantageous, for example, by allowing the wearer to independently adjust the pressure at either end of the block.

Figure 6:
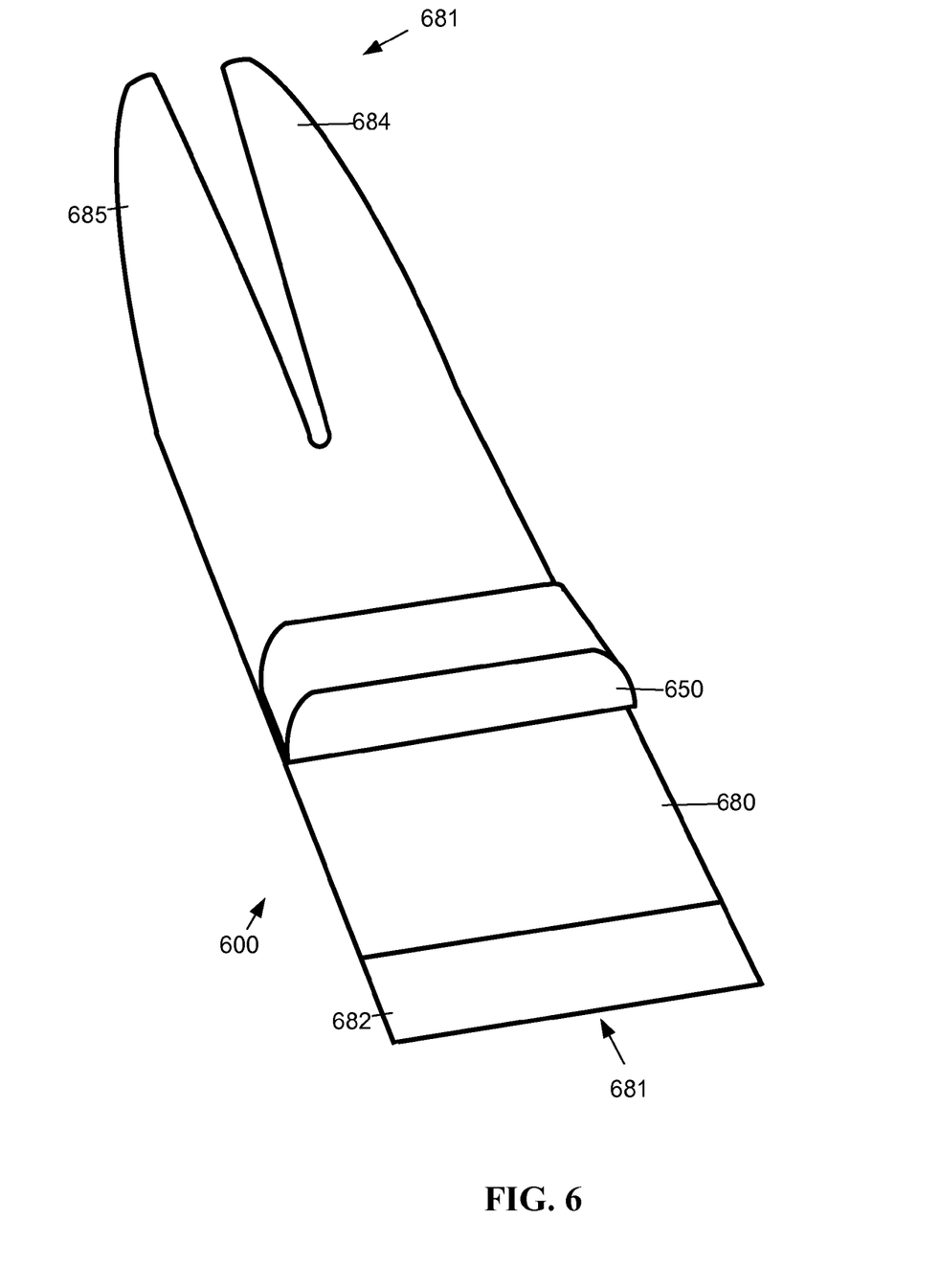
FIG. 6 is schematic diagram of a sixth exemplary embodiment of a plantar fasciitis arch support device including a partially split strap portion.

FIG. 6 shows a sixth embodiment of a PFAS device 600 including a partially split portion of a strap 680. Under the sixth embodiment, a block 650 is configured to be held against the foot of a wearer by the strap 680. The block 650 may be substantially similar to any of the blocks of the first, second, third, fourth and fifth embodiments, as described above.

The strap 680 attaches to the block 650. The strap 680 has a first end 681 having a strap attachment region 682. A second end 683 of the strap 680 is disposed substantially opposite the first end 681, on the other side of the block 650 from the first end 681. The second end 683 of the strap 680 is split into a first connecting portion 684 and a second connecting portion 685. The first connecting portion 684 and the second connecting portion 685 may each attach to the strap attachment region 682. The first connecting portion 684 and the second connecting portion 685 may be separately adjusted, for example, so the first connecting portion 684 is tighter or looser than the second connecting portion 685, corresponding to supplying more or less pressure by the block 650 to either plantar fascia attachment areas on the foot of the wearer.

The sixth embodiment may also provide versatility advantages, for example, being easily configured to be worn on the left foot or the right foot of the wearer. While the sixth embodiment is depicted as having the strap 680 connected to the base of the block 650, there is no objection to the strap 680 passing through a slot in the block 650, as per the fifth embodiment.

Method

A device for treating and preventing plantar fasciitis according to the present invention has been described above.

Figure 4:
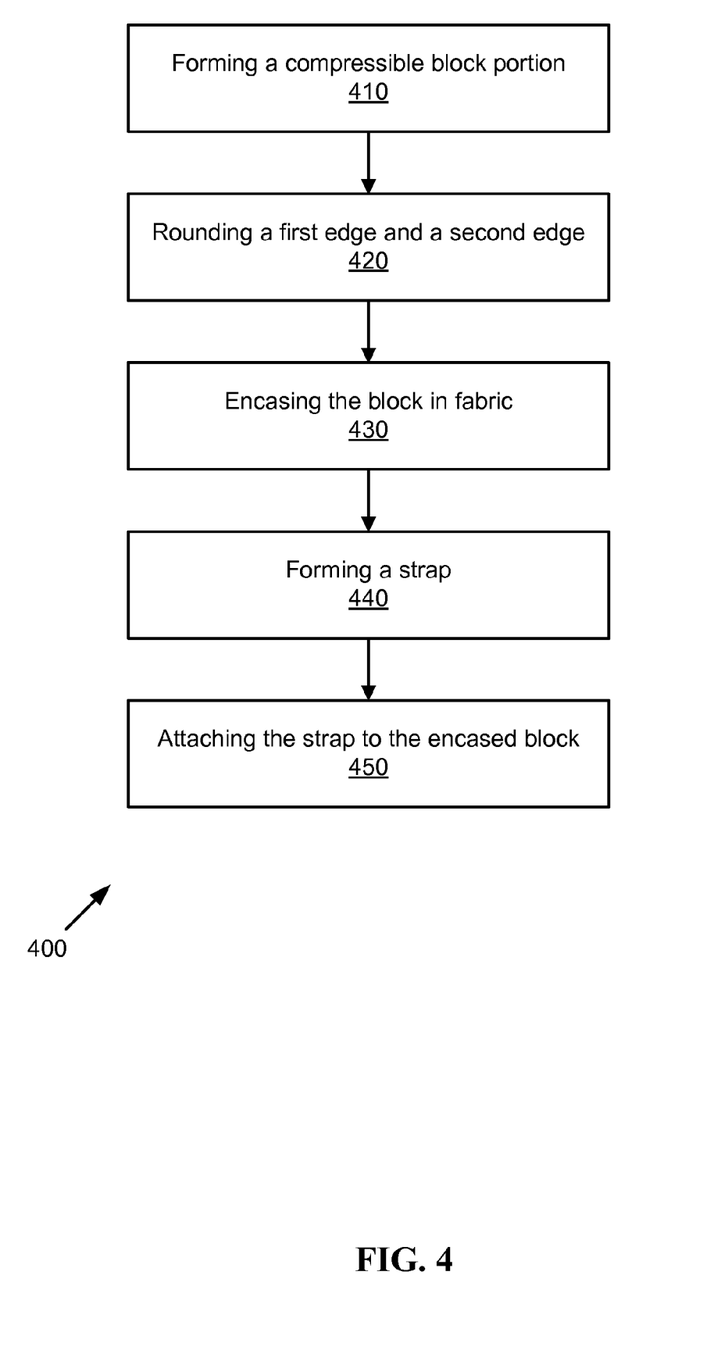
FIG. 4 is a flow chart of an exemplary embodiment of a method for making a plantar fasciitis arch support device.

A flow chart of an exemplary embodiment of a method 400 for making the present invention is shown in FIG. 4. It should be noted that any process descriptions or blocks in flow charts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

The step of forming a block portion is shown by block 410. As described above, the block may be partially compressible, yet rigid enough to maintain pressure against the plantar fasciitis. The first and second edges of the block portion are rounded, as shown by block 420. The block portion is at least partially encased in fabric, as shown by block 430. A strap is formed, as shown by block 440. Attaching the strap to the encased block is shown by block 450.

Returning to FIG. 3, the block 150 is placed beneath the foot, positioned between the calcaneus and the metatarsal head. The strap 180 is wrapped around the foot and the block 150 to hold the block 150 in place. The fabric strap 180 may be matched to the width of the block 150, and the ends of the strap 180 may be adhered to one another in order to hold the block 150 in place.

Intended Use

The PFAS device is an ergonomic compression device that administers a measured pressure along the tissue on the plantar surface of the foot for purpose of pain and inflammation relief. The PFAS device works by concentrating its compressive force at the attachment points of the fascia. This differs from current conventional splints that use a dorsiflexion force of the foot and ankle complex to stretch the plantar fascia and Achilles. There may be many advantages from foregoing the Achilles stretch.

In the morning upon waking, the wearer of the PFAS device is encouraged to wear the PFAS device for his or her initial steps. Though daytime movement lengthens the plantar fascia, it generally contracts during nighttime hours. When the tendon is static, it binds and develops scar tissue. In the first morning steps of the wearer, the fascia may stretch abruptly and the scar tissue may be torn. The PFAS device eases morning pain by keeping the tendon lengthened throughout the night, and when the wearer takes his or her first steps with the device still affixed, the tendon has time to gently stretch. Thus, the protocol suggested for using the PFAS device is to wear it both in sleep and during the first daytime steps. The PFAS device is not advised to be worn during the day, unless the wearer expects extended periods of little movement. The device may be custom fitted to any wearer.

An example treatment regime for the device described is to don the device on the afflicted foot just before bed. At first use, it is suggested that the wearer strap the device to their foot at a tightness that is comfortable to them, and tighten the device gradually over the course of several nights. The device should be tightened enough to provide a gentle, comfortable stretch, but not so much that the wearer is in pain.

In the morning upon waking, the wearer is encouraged to wear the device for his or her initial steps, as described above. The wearer is also advised to wear the device during prolonged periods of low-activity, such as sitting at a desk during the workday. This will keep the plantar fascia engaged in stretch to avoid tendon binding, scar tissue formation, and subsequent pain upon standing and stretching the fascia.

In summary, exemplary embodiments of a PFAS device for treating plantar fasciitis and exemplary methods for making a PFAS device have been presented. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A foot wearable ergonomic compression device comprising:
   a compressible block further comprising:
      a top comprising:
         a heel contact region; and
         a metatarsophalangeal contact region;
      a base substantially opposite said top;
      a first side disposed substantially adjacent said top and said base; and
      a second side opposite said first side disposed substantially adjacent said top and said base; and
   a strap attached to said compressible block, wherein said strap is configured to hold said compressible block-top adjacent to the foot,
   wherein said heel contact region consists of a first convex rounded edge configured to provide pressure at a first plantar fascia attachment point of the foot and said metatarsophalangeal contact region consists of a second convex rounded edge configured to provide pressure at a second plantar fascia attachment point of the foot, and wherein said strap has a width corresponding to a length of said block extending from said heel contact region to said metatarsophalangeal contact region and said strap is further configured to position said first convex rounded edge adjacent to said first plantar fascia attachment point and to position said second convex rounded edge adjacent to said second plantar fascia attachment point, and said length of said block is shorter than a length of the foot.

2. The device of claim 1, wherein said compressible block further comprises:
   a core portion; and
   an encasing at least partially wrapped around said core portion.

3. The device of claim 1, wherein said strap further comprises:
   a first end; and
   a second end, substantially opposite said first end,
   wherein said first end is configured to attach to said second end.

4. The device of claim 3, wherein said second end is split into a first connecting portion and a second connecting portion.

5. The device of claim 1, wherein said strap is non-removably attached to said base of said compressible block.

6. The device of claim 1, wherein said strap is removably attached to said base of said compressible block.

7. The device of claim 1, further comprising a slot disposed between said first side and said second side of said compressible block.

8. The device of claim 7, wherein said strap passes through said slot.

9. The device of claim 7, further comprising a bottom layer adjacent to said base of said compressible block.

10. The device of claim 9, wherein bottom layer comprises a substantially non-skid material.

11. The device of claim 1, wherein a first portion of said compressible block comprises a compressible material, and a second portion of said compressible block comprises a substantially non-compressible material.

12. The device of claim 1, wherein said compressible block is configured to apply less pressure elsewhere upon the foot than at said first plantar fascia attachment point of the foot and said second plantar fascia attachment point of the foot.

13. A foot wearable ergonomic compression device comprising:
a compressible block further comprising:
a top comprising:
a heel contact region; and
a metatarsophalangeal contact region; and
a base substantially opposite said top;
a first side disposed substantially adjacent said top and said base; and
a second side opposite said first side disposed substantially adjacent said top and said base;
a first strap portion attached to said first side; and
a second strap portion attached to said second side,
wherein said first strap portion and said second strap portion have a width corresponding to a length of said block extending from said heel contact region to said metatarsophalangeal contact region and are configured to wrap around the foot, said first strap portion is configured to attach to said second strap portion, to hold said compressible block adjacent to the foot, and said heel contact region comprises a first convex rounded edge configured to provide pressure at a first plantar fascia attachment point of the foot and said metatarsophalangeal contact region comprises a second convex rounded edge configured to provide pressure at a second plantar fascia attachment point of the foot, said first strap portion and said second strap portion are further configured to position said first convex rounded edge adjacent to said first plantar fascia attachment point and to position said second convex rounded edge adjacent to said second plantar fascia attachment point, and said length of said block is shorter than a length of the foot.

14. The device of claim 13, wherein said second strap portion is split into a first connecting portion and a second connecting portion.

15. The device of claim 13, wherein a first portion of said compressible block comprises a compressible material, and a second portion of said compressible block comprises a substantially non-compressible material.

16. The device of claim 13, further comprising a bottom layer adjacent to said base of said compressible block.

17. The device of claim 13, wherein said bottom layer comprises a substantially non-skid material.

18. The device of claim 13, wherein said compressible block further comprises:
a core portion; and
an encasing at least partially wrapped around said core portion.

19. The device of claim 13, wherein said compressible block is configured to apply less pressure elsewhere upon the foot than at said first plantar fascia attachment point of the foot and said second plantar fascia attachment point of the foot.

20. A method for manufacturing a foot wearable ergonomic compression device comprising the steps of:
forming a substantially rectangular compressible block, wherein said block is sized to extend from the ball of the foot to the heel of the foot;
forming a first convex edge of said block positionable at or near a first plantar fascia attachment point of the foot and a second convex edge of said block postionable at or near a second plantar fascia attachment point of the foot, wherein said first convex edge corresponds to the ball of the foot, and said second convex edge corresponds to said heel of the foot; and
forming a strap of material having a width corresponding to a length of said block and sized to surround said foot and said block held adjacent to a sole of the foot.

21. The method of claim 20, further comprising the step of attaching said strap to said block.

22. The method of claim 20, further comprising the step of wrapping said block with an encasing, wherein said encasing is sized to substantially surround said block.

23. The method of claim 20, further comprising the step of forming a bottom layer adjacent to said compressible block.

24. The method of claim 23, wherein said bottom layer comprises a substantially non-skid material.

25. The method of claim 20, wherein a first portion of said compressible block comprises a compressible material, and a second portion of said compressible block comprises a substantially non-compressible material.

* * * * *